United States Patent
Satoh et al.

(10) Patent No.: US 11,557,372 B2
(45) Date of Patent: Jan. 17, 2023

(54) PREDICTION DEVICE, GENE ESTIMATION DEVICE, PREDICTION METHOD, AND NON-TRANSITORY RECORDING MEDIUM

(71) Applicant: NEC Corporation, Tokyo (JP)

(72) Inventors: Mineto Satoh, Tokyo (JP); Soichiro Araki, Tokyo (JP); Kenichiro Fujiyama, Tokyo (JP); Tetsuri Ariyama, Tokyo (JP); Tan Azuma, Tokyo (JP)

(73) Assignee: NEC CORPORATION, Tokyo (JP)

( * ) Notice: Subject to any disclaimer, the term of this patent is extended or adjusted under 35 U.S.C. 154(b) by 499 days.

(21) Appl. No.: 16/620,706

(22) PCT Filed: Jun. 30, 2017

(86) PCT No.: PCT/JP2017/024229
§ 371 (c)(1),
(2) Date: Dec. 9, 2019

(87) PCT Pub. No.: WO2019/003441
PCT Pub. Date: Jan. 3, 2019

(65) Prior Publication Data
US 2021/0142865 A1    May 13, 2021

(51) Int. Cl.
*G16B 20/00* (2019.01)
*G16B 30/00* (2019.01)

(52) U.S. Cl.
CPC .............. *G16B 20/00* (2019.02); *G16B 30/00* (2019.02)

(58) Field of Classification Search
CPC .................................. G16B 30/00; G16B 20/00
See application file for complete search history.

(56) References Cited

U.S. PATENT DOCUMENTS

2008/0160054 A1    7/2008   Heinz et al.
2010/0016352 A1*   1/2010   Li ..................... A61K 31/35
                                              514/312
(Continued)

FOREIGN PATENT DOCUMENTS

CA    2364569 A1    9/2000
EP    3188060 A1    7/2017
(Continued)

OTHER PUBLICATIONS

Japanese Office Action for JP Application No. 2019-526116 dated Jan. 12, 2021 with English Translation.
(Continued)

*Primary Examiner* — Eliyah S. Harper

(57) ABSTRACT

Provided are a prediction device and the like capable of more accurately simulating an analysis target. The prediction device generates function information for a gene sequence of a living body to be an analysis target based on first model information representing a relevance between sequence information and the function information, the sequence information representing the gene sequence of the analysis target, the function information representing a function potentially expressed by the gene sequence; and generates prediction information representing observation information predicted for the analysis target based on second model information and the function information, the second model information representing a relevance among the function information of the living body, environment information representing an environment around the living body, and the observation information observed for the living body, the function information being generated for the gene sequence of the analysis target.

8 Claims, 5 Drawing Sheets

(56) References Cited

U.S. PATENT DOCUMENTS

| | | | | |
|---|---|---|---|---|
| 2010/0330567 | A1* | 12/2010 | Hoon | C12Q 1/6886 435/6.13 |
| 2012/0109615 | A1* | 5/2012 | Yun | G16B 40/20 703/11 |
| 2015/0184247 | A1* | 7/2015 | Giancotti | C12Q 1/6886 435/375 |
| 2015/0368322 | A1* | 12/2015 | McAdow | A61P 31/00 530/387.3 |
| 2018/0060482 | A1* | 3/2018 | Nadauld | G06N 20/00 |
| 2018/0077892 | A1* | 3/2018 | Kaeppler | A01H 5/10 |
| 2019/0110450 | A1* | 4/2019 | Serreze | A01K 67/0276 |
| 2021/0027855 | A1* | 1/2021 | Zhou | G16B 25/10 |
| 2021/0142865 | A1* | 5/2021 | Satoh | G16B 30/00 |

FOREIGN PATENT DOCUMENTS

| | | |
|---|---|---|
| JP | 2002-537806 A | 11/2002 |
| JP | 2003-523746 A | 8/2003 |
| JP | 2005-309877 A | 11/2005 |
| JP | 2006-236153 A | 9/2006 |
| JP | 2010-222300 A | 10/2010 |
| JP | 4791737 B2 | 10/2011 |
| WO | WO-2001/18177 A1 | 3/2001 |
| WO | WO-2016/031174 A1 | 3/2016 |
| WO | WO-2016/194379 A1 | 12/2016 |

OTHER PUBLICATIONS

Extended European Search Report issued in European Patent Application No. 17915679.9, dated May 26, 2020, 8 pages.

International Search Report corresponding to PCT/JP2017/024229 dated Sep. 19, 2017 (2 pages).

Written Opinion corresponding to PCT/JP2017/024229 dated Sep. 19, 2017 (5 pages).

* cited by examiner

PREDICTION DEVICE, GENE ESTIMATION DEVICE, PREDICTION METHOD, AND NON-TRANSITORY RECORDING MEDIUM

CROSS REFERENCE TO RELATED APPLICATIONS

This application is a national stage application of International Application No. PCT/JP2017/024229 entitled "Forecasting Device, Forecasting Method, Storage Medium Stored With Forecasting Program, and Genetic Inference Device" filed on Jun. 30, 2017, the disclosures of which are hereby incorporated by reference in their entirety.

TECHNICAL FIELD

The present invention relates to a prediction device and the like that predict an event for an analysis target.

BACKGROUND ART

PTL 1 discloses a simulation device for numerically simulating an event that occurs in a real world by employing a computer. The simulation device predicts a state of an analysis target based on model information representing a state of the analysis target. The simulation device updates the model based on the predicted state and observation information observed for the analysis target.

PTL 2 discloses a method of predicting values of variables relating to a crop, and the like.

CITATION LIST

Patent Literature

PTL 1: PCT International Publication No. 2016/194379
PTL 2: PCT International Publication No. 2001/18177

SUMMARY OF INVENTION

Technical Problem

However, even when any of the devices disclosed in PTLs 1 to 2 is employed, a prediction result is not necessarily accurate. A reason for this is that model information based on which a state or the like of an analysis target is simulated is not necessarily accurate. Specifically, since the model information often includes an error, a result of simulation based on the model information is not necessarily accurate.

In view of the above, one of objective of the present invention is to provide a prediction device and the like capable of more accurately simulating an analysis target.

Solution to Problem

As an aspect of the present invention, a prediction device includes:
  first model processing means for generating function information for a gene sequence of a living body to be an analysis target based on first model information representing a relevance between sequence information and the function information, the sequence information representing the gene sequence of the analysis target, the function information representing a function potentially expressed by the gene sequence; and
  second model processing means for generating prediction information representing observation information predicted for the analysis target based on second model information and the function information, the second model information representing a relevance among the function information of the living body, environment information representing an environment around the living body, and the observation information observed for the living body, the function information being generated for the gene sequence of the analysis target by the first model processing means.

In addition, as another aspect of the present invention, a prediction method includes:
  generating function information for a gene sequence of a living body to be an analysis target based on first model information representing a relevance between sequence information and the function information, the sequence information representing the gene sequence of the analysis target, the function information representing a function potentially expressed by the gene sequence; and
  generating prediction information representing observation information predicted for the analysis target based on second model information and the function information, the second model information representing a relevance among the function information of the living body, environment information representing an environment around the living body, and the observation information observed for the living body, the function information being generated for the gene sequence of the analysis target.

In addition, as another aspect of the present invention, a prediction program causes a computer to achieve:
  a first model processing function for generating function information for a gene sequence of a living body to be an analysis target based on first model information representing a relevance between sequence information and the function information, the sequence information representing the gene sequence of the analysis target, the function information representing a function potentially expressed by the gene sequence; and
  a second model processing function for generating prediction information representing observation information predicted for the analysis target based on second model information and the function information, the second model information representing a relevance among the function information of the living body, environment information representing an environment around the living body, and the observation information observed for the living body, the function information being generated for the gene sequence of the analysis target by the first model processing function.

Furthermore, the object is also achieved by a computer-readable recording medium that records the program.

Advantageous Effects of Invention

A prediction device and the like according to the present invention are able to more accurately simulate an analysis target.

EXAMPLE EMBODIMENT

Figure 1:
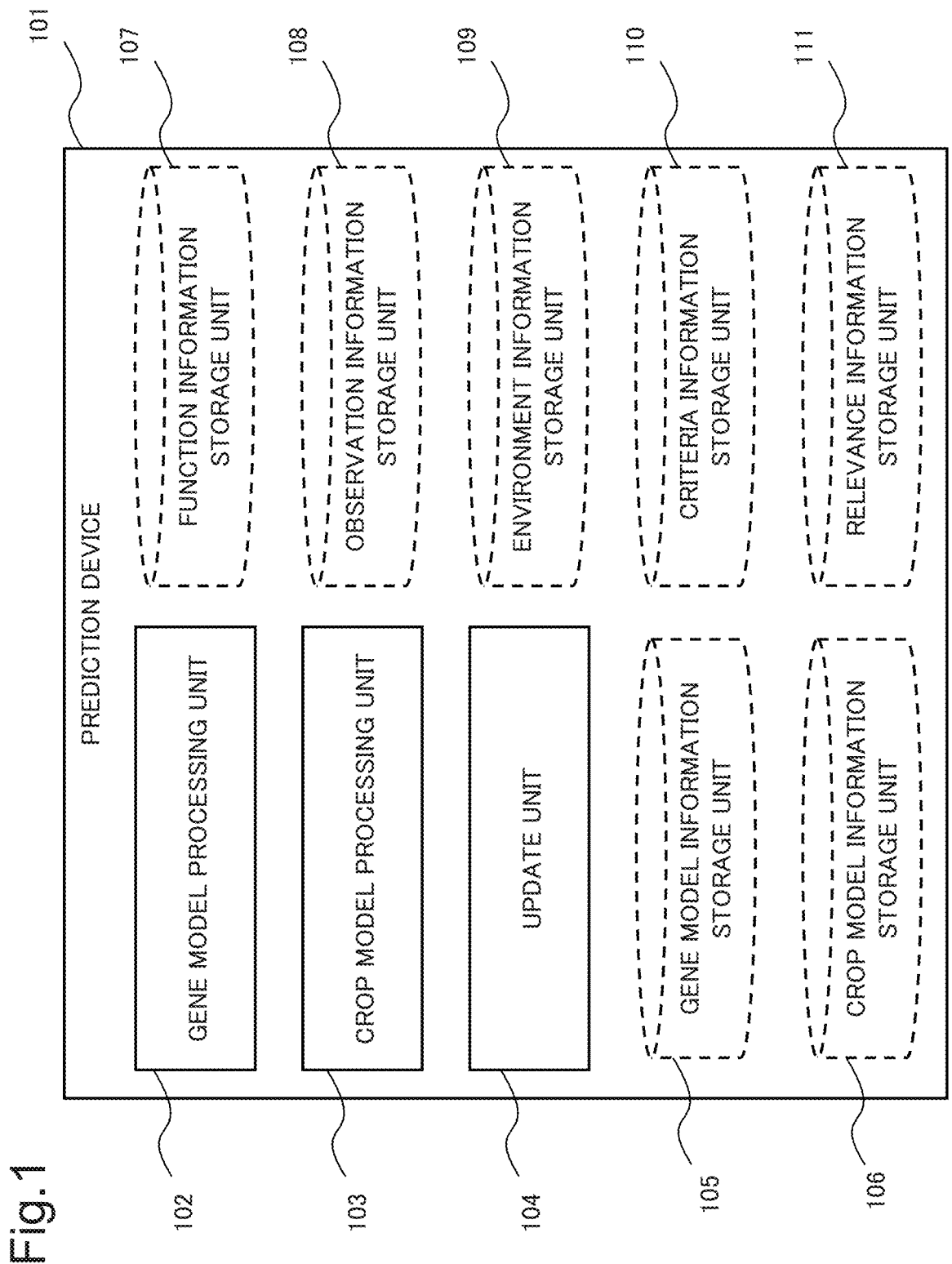
FIG. 1 is a block diagram illustrating a configuration of a prediction device according to a first example embodiment of the present invention.

First, to facilitate understanding of the present invention, an issue to be solved by the present invention will be described in detail.

Numerical simulation relating to an analysis target is performed, based on model information representing a relevance between input information being an input to the analysis target, and output information to be output by the analysis target. The model information is, for example, information that represents a relevance that is physically established between the input information and the output information with a partial differential equation. Simulation performed by an information processing device includes generating simultaneous linear equations by discretizing the partial differential equation, solving the generated simultaneous linear equations, and, thereby, calculating a state of the analysis target.

However, an error may occur in representing an event (e.g., a motion, or a change in state) occurred for an analysis target with using model information and the occurred error may cause a gap between a simulation result and observation information that is actually observed. For example, when an analysis target is a living body such as a plant, a gap may occur between observation information that is actually observed for the analysis target and prediction information representing a prediction result relating to the observation information (specifically, information representing a result predicted for observation information).

The inventors of the present application have found that, when an analysis target is a living body such as a plant, a gap is likely to occur between observation information (event) observed for the analysis target and an event predicted by simulation. Further, the inventors of the present application have found that one of factors causing such gap is that, even when a living body of same species is an analysis target, gene sequences of the individual analysis target are different, however, model information in simulation does not reflect such difference in gene sequences. Furthermore, the inventors of the present application have found an issue that, even when the different living bodies have a common gene sequence, growth states are different depending on an environment of the living bodies and model information does not reflect such condition. The inventors of the present application have found an issue on such condition and derived means for solving the issue.

Next, terms to be used in example embodiments of the present invention will be described.

It is assumed that a parameter denotes a certain storage area in a storage device (storage unit). Processing of setting a value to a parameter is processing of storing data in the storage area identified by the parameter. Further, a value relating to a variable (parameter) is also referred to as a "value of a variable (parameter)" or a "variable (parameter) value". A value of a parameter represents a value stored in the storage area identified by the parameter. For convenience of description, a value A of a parameter may be simply referred to as a "parameter A".

Further, when a value of a random variable S is C, a conditional probability P with which a random variable T is D is expressed by Formula A.

$$P(T=D|S=C) \qquad \text{(Formula A).}$$

Further, as far as there is no misunderstanding, it is assumed that a value of a random variable is expressed by using a suffix of the random variable. In this case, it is possible to express Formula A by Formula B.

$$P(T=TD|S=SC) \qquad \text{(Formula B).}$$

Furthermore, for convenience of description, as far as there is no misunderstanding, it is assumed that the random variables S and T are omitted. In this case, it is possible to express Formula B by Formula C.

$$P(TD|SC) \qquad \text{(Formula C).}$$

Hereinafter, a simulation target is referred to as an "analysis target". Information to be observed for the analysis target by a sensor or the like is referred to as "observation information". Information predicted by simulating the analysis target is referred to as "prediction information". Further, when the analysis target such as a plant is identified based on a gene sequence, each of the analysis targets is referred to as an "individual".

Hereinafter, example embodiments for implementing the present invention capable of solving an above-described issue will be described in detail with reference to the drawings.

First Example Embodiment

A configuration of a prediction device 101 according to a first example embodiment of the present invention will be described in detail with reference to FIG. 1. FIG. 1 is a block diagram illustrating a configuration of the prediction device 101 according to the first example embodiment of the present invention.

The prediction device 101 according to the first example embodiment includes a gene model processing unit (gene model processor) 102, a crop model processing unit (crop model processor) 103, and an update unit (updater) 104. The prediction device 101 may further include a gene model information storage unit 105, a crop model information storage unit 106, a function information storage unit 107, an observation information storage unit 108, an environment information storage unit 109, a criteria information storage unit 110, and a relevance information storage unit 111.

In the following description, for convenience of description, it is assumed that an analysis target is a plant (crop) to be grown in a field. The analysis target, however, is not limited to a plant, and any living body is applicable. Likewise, for convenience of description, a processing target of the prediction device 101 is described by using crop model information, the crop model processing unit 103, and the crop model information storage unit 106. However, the processing target of the prediction device 101 is not limited to crop model information. In the following description, more generalized crop model information may be referred to as "second model information". Likewise, a crop model processing unit may be referred to as a "second model processing unit" ("second model processor"). A crop model information storage unit may be referred to as a "second model information storage unit".

The environment information storage unit 109 stores environment information relating to an environment around a plant. The environment information is, for example, information representing an amount of rainfall in a field, an amount of moisture contained in soil in the field, an amount of nitrogen contained in the soil, a temperature in the field, and hours of daylight in the field. The environment information may be, for example, information representing an amount of irrigation performed in the field. The environment information may include information different from the above-described examples. The environment information may be environment information relating to an environment around an individual.

The observation information storage unit 108 stores observation information Y observed for a plant. The observation information is, for example, a leaf area index relating to a plant, a size of the plant, the number of leaves, a leaf size, and a size of a crop. The observation information may be observation information observed for an individual. The observation information may be information acquired by employing a sensor or the like, or may be information calculated based on observed information. The observation information is not limited to the above-described examples.

The function information storage unit 107 stores function information $C_{crop}$ representing a function potentially expressed by a gene sequence of a plant (or an individual), or an event that occurs by expression of the function. Specifically, the function information $C_{crop}$ is information relating to a function potentially expressed by a gene sequence. The function information $C_{crop}$ may be information in which sequence information representing the gene sequence and information representing the function (or the event) are associated with each other. The function information $C_{crop}$ may be information in which the sequence information, information representing the function (or the event), and environment information relating to the plant (or an individual) when the function (or the event) occurs are associated with one another.

The function information $C_{crop}$ may be information representing the function itself, or may be information representing an event that occurs by the function. For example, when an individual has a certain gene sequence, the function information $C_{crop}$ may be information representing a state that roots are spread in soil (e.g., a volume of an area where roots are spread), or may be information representing an event that occurs by spread of roots (e.g., a water absorption rate). The function information $C_{crop}$ may be information representing a size of a plant, a period until a crop is harvested, a color of a crop, a size of a crop, and the like. The function information $C_{crop}$ may be information representing a state that a plant expressing the function is grown depending on an environment around the plant. For example, when a certain amount of rain falls on soil where a plant having widely spread roots is grown, the function information $C_{crop}$ may be information representing an amount of moisture to be absorbed by the plant through the roots. In this case, gene model information is information representing a relevance between sequence information $X_{gene}$ relating to a plant, environment information relating to an environment around the plant, and the function information $C_{crop}$. The function information $C_{crop}$ may be information registered in a general nucleic acid sequence database, or may be information acquired by observing an individual including a gene sequence. The function information $C_{crop}$ is not necessarily only one piece of information, but may include a plurality of pieces of information. The gene model information and the function information $C_{crop}$ are not limited to the above-described examples.

The gene model information storage unit 105 stores gene model information (hereinafter, also referred to as "first model information") representing a relevance between sequence information $X_{gene}$ representing a gene sequence of a plant and the function information $C_{crop}$. The gene model information may be information representing a relevance among sequence information $X_{gene}$ relating to a plant, environment information representing an environment around the plant, and function information $C_{crop}$ relating to the plant. The gene model information may be information with which a plant identifier (hereinafter, an identifier is referred to as an "ID") identifying the plant is further associated. For example, it is possible to acquire function information relating to the certain plant by applying the gene model information to a gene sequence of a certain individual and environment information representing an environment around the individual.

In the following description, for convenience of description, environment information to be input to gene model information is referred to as "first environment information $\theta_{env}$".

The gene model information will be described with reference to an example.

For convenience of description, it is assumed that sequence information $X_{gene}$ represents a gene sequence which influences a condition on spread of roots. When an individual grown in a field has a gene sequence that roots spread widely, the individual roots more widely in soil, as growing, than an individual without the gene sequence. Herein, it is assumed that a little rain condition occurs in a field. The individual having a gene sequence that roots spread widely grows large, since the individual can absorb a sufficient amount of moisture even in a little rain condition. On the other hand, the individual without the gene sequence that roots spread widely cannot grow large, since the individual cannot absorb a sufficient amount of moisture in a little rain condition. In this case, the function information $C_{crop}$ is information representing water absorbing capacity of the individual, for example. The function information $C_{crop}$ may be information representing a stress resistance or the like of the individual. The first environment information $\theta_{env}$ is an amount of rainfall in a field. A size of an individual (one example of the function information $C_{crop}$) is determined in accordance with a function that is expressed by sequence information $X_{gene}$ of the individual, the first environment information $\theta_{env}$ relating to an environment around the individual, and the like.

The crop model information storage unit 106 stores crop model information (one example of "second model information") representing a relevance among function information $C_{crop}$ relating to a plant, environment information relating to an environment around the plant, and observation information Y (or prediction information relating to the observation information) that is actually observed for the plant (or an individual). Hereinafter, for convenience of description, in description of the crop model information, observation information and prediction information are generically referred to as "observation information".

In the following description, for convenience of description, environment information to be input to the crop model information is referred to as "second environment information $\theta2_{env}$". Further, the second environment information $\square2_{env}$, and the first environment information $\theta_{env}$ are generically referred to as "environment information".

The second environment information $\theta2_{env}$ may be information of a same type as the first environment information $\theta_{env}$, or may be information of a different type. The crop model information will be described with reference to an example.

For convenience of description, it is assumed that the function information $C_{crop}$ relating to a plant is information representing water absorbing capacity of the plant. Further, it is assumed that the observation information Y is a normalized difference vegetation index (NDVI) relating to the plant.

It is possible to calculate a vegetation index, for example, based on an image captured at an angle of view including a field from a flying object such as an artificial satellite or a drone. For example, a camera in the flying object captures such image, while the flying object hovering above a field. For example, the vegetation index is calculated in accordance with processing expressed by Formula 1, based on a reflectivity R of red light in a visible range and a reflectivity IR in a near infrared range observed in the vicinity of a field.

$$NDVI=(IR-R)\div(IR+R) \qquad \text{(Formula 1)},$$

where NDVI represents that vegetation is dense, as the NDVI has a large plus value.

For example, a plant sprouts in spring, and becomes leafy as growing. When summer comes, the growth of the plant stops, and as a result of blooming, the vegetation index (exemplified in Formula 1) is lowered. Then, a fruit (specifically, a crop) starts ripening, and in fall, the color of the leaves changes (or the leaves start to fall). Then, a lowering degree of the vegetation index (exemplified in Formula 1) increases. In this example, the second environment information $\theta2_{env}$ is information such as hours of daylight in a field, or a temperature around the field. Therefore, in this example, the crop model information is a model representing a relevance between hours of daylight, a temperature around a field, and water absorbing capacity of a plant (one example of the function information $C_{crop}$); and a vegetation index (one example of the observation information Y) relating to the plant.

The relevance information storage unit 111 stores relevance information that associates sequence information $x_{gene}$ with observation information Y observed for an individual having a gene sequence represented by the sequence information $x_{gene}$. The relevance information may be information that associates sequence information $x_{gene}$ with prediction information such that observation information Y relating to an individual having a gene sequence represented by the sequence information $x_{gene}$ is predicted. Alternatively, the relevance information may be information that associates observation information Y observed for an individual with sequence information $x_{gene}$ representing a gene sequence estimated for the individual. In the following description of relevance information, observation information and prediction information are generically referred to as observation information. The relevance information is not limited to the above-described examples.

The criteria information storage unit 110 stores criteria information representing a selection condition that is a basis of selecting specific relevance information among relevance information stored in the relevance information storage unit 111. The criteria information is, for example, a criterion relating to stability such that a deviation range from observation information Y is narrow, a criterion relating to tolerance such that a gap between observation information Y and prediction information is small, a criterion such that a range of observation information Y is within a criteria range, or the like. The criteria information is, for example, a criterion such that a similarity degree to observed observation information Y satisfies a predetermined condition. In this case, the criteria information is a criterion for selecting observation information similar to observed observation information Y.

Figure 2:
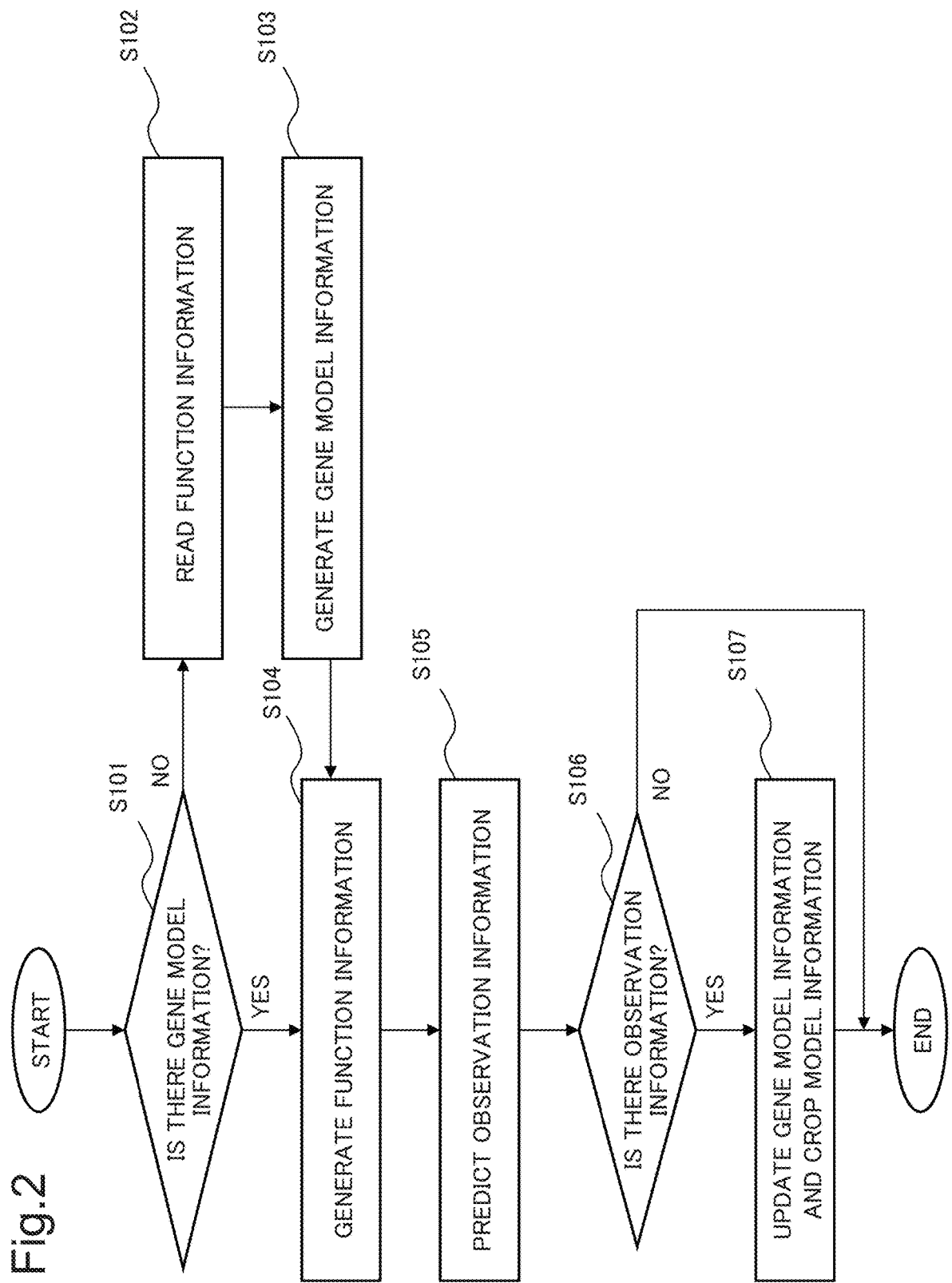
FIG. 2 is a flowchart illustrating a flow of processing in the prediction device according to the first example embodiment.

Next, processing in the prediction device 101 according to the first example embodiment of the present invention will be described in detail with reference to FIG. 2. FIG. 2 is a flowchart illustrating a flow of processing in the prediction device 101 according to the first example embodiment.

The gene model processing unit 102 receives a plant ID for identifying a plant being an analysis target.

Next, the gene model processing unit 102 determines whether or not gene model information for a plant identified by the plant ID is stored in the gene model information storage unit 105 (Step S101). The gene model information is information representing a relevance among sequence information $x_{gene}$ representing a gene sequence of an individual being the plant, first environment information $\theta_{env}$ representing an environment around the individual, and function information $C_{crop}$ relating to the individual.

When the gene model information relating to the plant identified by the plant ID is not stored in the gene model information storage unit 105 (NO in Step S101), the gene model processing unit 102 reads, from the function information storage unit 107, function information $C_{crop}$ which associates sequence information, environment information, and information relating to a function (or the event) with one another (Step S102). The gene model processing unit 102 generates gene model information based on the read function information $C_{crop}$ (Step S103). Processing of generating gene model information by the gene model processing unit 102 is, for example, processing of statistically acquiring a relevance that is established between known sequence information $x_{gene}$ and known function information $C_{crop}$, or processing of determining values of parameters included in the below-described Formula 2 (or Formula 3), based on known sequence information $x_{gene}$ and known function information $C_{crop}$. The processing of generating gene model information is not limited to the above-described examples.

When the gene model information relating to the plant identified by the plant ID is stored in the gene model information storage unit 105 (YES in Step S101), the gene model processing unit 102 reads the gene model information from the gene model information storage unit 105.

The gene model processing unit 102 receives, from an outside, sequence information $x_{gene}$ representing a gene sequence of a plant and first environment information $\theta_{env}$ relating to an environment around the plant. The gene model processing unit 102 generates function information $C_{crop}$ relating to the plant by applying predetermined processing exemplified by the gene model information $f_{gp}$ (Formula 2) to the sequence information $x_{gene}$ and the first environment information $\theta_{env}$ relating to the surrounding environment (Step S104).

$$C_{crop}=f_{gp}(x_{gene},\theta_{env}) \qquad \text{(Formula 2)}.$$

The predetermined processing is, for example, processing of predicting a target variable relating to certain explanatory variables by using model information generated in accordance with a supervised learning method. In this case, the explanatory variables are sequence information $x_{gene}$ relating to a plant and first environment information $\theta_{env}$ relating to an environment around the plant. The target variable is function information $C_{crop}$ relating to the plant. The gene model processing unit 102 generates function information $C_{crop}$ for the received first environment information $\theta_{env}$ and sequence information $x_{gene}$ by using gene model information generated by using sequence information relating to the plant, environment information, and function information as training data.

The predetermined processing is not limited to the supervised learning method, but may be a statistical method such as a semi-supervised learning method, Bayesian estimation, or a simulation method based on model information as described later with reference to Formulas 4 to 7. Further, the gene model information may include information (a parameter $\eta$ in Formula 3) representing an error that occurs when the above-described relevance is expressed by using model information. Furthermore, the gene model information may include a parameter different from the above-described parameter (such as the sequence information $x_{gene}$). The predetermined processing is not limited to the above-described examples.

Further, as exemplified in Formula 3, the gene model information $f_{gp}$ may be model information including the parameter $\eta$.

$$C_{crop} = f_{gp}(x_{gene}, \theta_{env}, \eta) \qquad \text{(Formula 3)}.$$

However, the parameter $\eta$ is information denoting an influence on an event that occurs in an analysis target such as a plant. In other words, the parameter $\eta$ is a parameter denoting a correction amount for the expressed gene model information (exemplified in Formula 2). The sequence information $x_{gene}$ does not necessarily represent a gene sequence of a plant, but may be estimation information relating to a gene sequence. The estimation information is estimation information relating to a gene sequence. Further, the first environment information $\theta_{env}$ denotes environment information. The parameter $\eta$ denotes, for example, a difference between function information to be calculated in accordance with crop model information (which will be described later with reference to Formula 4 or 6) based on observation information Y, and function information to be calculated in accordance with the gene model information (exemplified in Formula 2 or 3). The sequence information $x_{gene}$ and the first environment information $\theta_{env}$ may be determined following a certain probability distribution. Therefore, information on the parameter $\eta$ (specifically, a parameter denoting correction) is determined in terms of probability, and it is also possible to express the information by using a probability.

The gene model processing unit 102 may store the function information $C_{crop}$ generated in Step S104 in the function information storage unit 107. The gene model processing unit 102 inputs the generated function information $C_{crop}$ to the crop model processing unit 103.

The crop model processing unit 103 receives the function information $C_{crop}$ from the gene model processing unit 102. The crop model processing unit 103 receives a plant ID from an external device or the gene model processing unit 102. The crop model processing unit 103 receives, from an external device such as a soil sensor or a moisture sensor, second environment information $\theta 2_{env}$ relating to an environment around a plant identified by the plant ID. The crop model processing unit 103 reads, from the crop model information storage unit 106, crop model information relating to the plant identified by the plant ID. The crop model processing unit 103 applies processing (exemplified in Formula 4) represented by crop model information $g_{growth}$ to the received function information $C_{crop}$ and the second environment information $\theta 2_{env}$. By the processing, the crop model processing unit 103 calculates state information $x_{pheno}$ representing a state of a crop at a certain timing t, and predicts observation information Y at the certain timing t (specifically, generates prediction information), based on the calculated state information $x_{pheno}$ (Step S105).

$$x_{pheno}{}^t = g_{growth}(x_{pheno}{}^{t-1}, C_{crop}, \theta 2_{env}) \qquad \text{(Formula 4)}.$$

$$Y^t = h(x_{pheno}{}^t) \qquad \text{(Formula 5)}.$$

As exemplified in Formula 4, the crop model information $g_{growth}$ is information in which pieces of state information $x_{pheno}$ at a plurality of timings are associated with one another by using the function information $C_{crop}$ and the second environment information $\theta 2_{env}$. In the example exemplified in Formula 4, state information $x_{pheno}{}^t$ at a timing t, and state information $x_{pheno}{}^{t-1}$ at a timing (t−1) are associated with each other. For example, in accordance with the processing expressed in Formula 4, it is possible to predict the state information $x_{pheno}{}^t$ at the timing t, based on the state information $x_{pheno}{}^{t-1}$ at the timing (t−1), the second environment information $\theta 2_{env}$, and the function information $C_{crop}$.

As expressed in Formula 5, observation model information h is information representing a relevance between state information $x_{pheno}{}^t$ at a certain timing t, and observation information $Y^t$ at the certain timing. For example, the observation model information h exemplified in Formula 5 is information representing a relevance between state information $x_{pheno}{}^t$ at a timing t, and observation information $Y^t$ at the timing t. For example, the observation model information h may be model information to be expressed by employing an identity function (specifically, a function of calculating state information $x_{pheno}{}^t$ as observation information $Y^t$). In this case, the observation model information h is information representing a relevance "$Y^t = x_{pheno}{}^t$".

Hereinafter, the observation model information h is also referred to as "third model information".

Even in a condition that it is possible to acquire, as the state information $x_{pheno}$, vegetation of individuals, weights of the individuals, the number of the individuals, and ripeness of the individuals, the observation model information h exemplified in Formula 5 may be information in which only observation information observed at a timing t is associated. For example, when only vegetation of individuals, and the number of individuals are observed at a timing t, the observation model information exemplified in Formula 5 may be information in which only the vegetation of the individuals and the number of the individuals are associated.

Further, when crop model information relating to a certain living body differs among a plurality of regions (or locations), the observation information Y may be acquired by calculating an average value (or a weighted average value) of observation information to be calculated in accordance with each piece of the crop model information.

As expressed in Formula 6, the crop model information $g_{growth}$ may have, for example, a system noise $v^t$ denoting uncertainty of a timewise change (time development) relating to the state information $x_{pheno}$. The system noise $v^t$ denotes a system noise at a timing t. Likewise, as expressed in Formula 7, the observation model information h may have, for example, an observation noise $w^t$ representing uncertainty relating to the crop model information. The observation noise $w^t$ representing uncertainty is, for example, information representing a difference (or an error or a noise) included in information observed by an observation device such as a soil sensor or a moisture sensor, or information representing a difference (or an error or a noise) included in the observation model information h itself. The observation noise $w^t$ denotes an observation noise at a timing t.

$$x_{pheno}^t = g_{growth}(x_{pheno}^{t-1}, C_{crop}^t, \theta 2_{env}^t, v^t) \quad \text{(Formula 6)},$$

$$Y^t = h(x_{pheno}^t, w^t) \quad \text{(Formula 7)}.$$

However, it is assumed that each of the system noise $v^t$ and the observation noise $w^t$ is, for example, a value generated in accordance with a Gaussian distribution taking an average of 0 and a predetermined variance.

In the following description, the crop model information $g_{growth}$ exemplified in Formula 6 and the observation model information h exemplified in Formula 7 may be generically referred to as a "state space model". As described later, the state space model exemplified in Formulas 6 and 7 is updated, for example, based on the state information $x_{pheno}^t$ and the observation information $Y^t$ at a timing t.

Further, as exemplified in Formulas 6 and 7, information and noise in each piece of model information may change with time. Specifically, $C_{crop}^t$ is function information $C_{crop}$ at a timing t. $\theta 2_{env}^t$ is second environment information $\theta 2_{env}$ at a timing t.

An example of a processing method of updating the state space model exemplified in Formulas 6 and 7 is a processing method of data assimilation processing. The data assimilation processing includes calculation processing of a difference between observation information (specifically, prediction information) to be calculated based on a plurality of various sets and actually observed observation information for a timing t. The set includes information such as the function information $C_{crop}^t$ and the second environment information $\theta 2_{env}^t$. When the plurality of sets include information to be generated by using a certain random number, it is also possible to regard that the difference (specifically, a system noise and an observation noise) is generated following a certain probability distribution. Hereinafter, one set may be referred to as an "ensemble", and a plurality of various sets may be referred to as an "ensemble set". Further, crop model information may include a parameter other than the above-described parameters (such as the function information $C_{crop}$).

The gene model information $f_{gp}$ (exemplified in Formula 2 or 3), and the crop model information $g_{growth}$ (exemplified in Formula 4) may be generated, for example, based on information such as a partial differential equation representing a relevance between a state relating to an analysis target, and observation information observed for the analysis target. The partial differential equation is not necessarily one equation, but may be a plurality of equations. The partial differential equation is discretized, for example, in accordance with a discretization method such as a finite element method. As a result, simultaneous linear equations are generated. The gene model information $f_{gp}$ (exemplified in Formula 2 or 3), and the crop model information $g_{growth}$ (exemplified in Formula 4) conceptually represent a processing procedure of calculating a solution of the simultaneous linear equations in accordance with a solution procedure such as an iteration method.

As expressed in Formula 8, an occurrence probability of state information $x_{pheno}^t$ in case of occurrence of function information $C_{crop}^t$ at a timing t can be a prediction probability when the function information $C_{crop}^t$ and the second environment information $\theta 2_{env}^t$ occurs.

$$p(x_{pheno}^t | x_{pheno}^{t-1}, C_{crop}^t, \theta 2_{env}^t) \quad \text{(Formula 8)}.$$

A value of the prediction probability expressed in Formula 8 can be obtained, for example, in accordance with an ensemble simulation. The ensemble simulation executes iteration processing for a plurality of sets. The iteration processing includes calculating function information $C_{crop}$ in accordance with the processing expressed in Formula 3 (or Formula 2) and calculating state information $x_{pheno}^t$ with respect to the calculated function information $C_{crop}$ in accordance with Formula 6 (or Formula 4).

An example of the ensemble simulation is an analytical method that includes selecting function information $C_{crop}$ following a normalized (Gaussian) distribution and predicting state information $x_{pheno}^t$ in accordance with Formula 6 (or Formula 4) for a value of the selected function information $C_{crop}$ (specifically, generating prediction information relating to the observation information). Alternatively, an example of the ensemble simulation includes calculating, as an average, $C_{crop}$ in accordance with the processing exemplified in Formula 3 (or Formula 2), adding, as a noise, a random number having a predetermined distribution in accordance with Formula 6 (or Formula 4) to the calculated value, and, thereby, generating an ensemble (an ensemble member). An ensemble set (exemplified in Formula 9) is generated by generating an ensemble (ensemble member) for each of a plurality of random numbers having the predetermined distribution. The ensemble simulation may be a method of generating prediction information relating to state information $x_{pheno}^t$, and observation information Y relating to the state information $x_{pheno}^t$ in accordance with the processing expressed in Formula 4 (or Formula 6) for each of ensemble members included in the generated ensemble set.

$$\{x_{pheno,k}^{t-1}, C_{crop,k}^t, \theta 2_{env,k}^t\} \quad \text{(Formula 9)},$$

where k (k denotes a natural number where $1 \leq k \leq N$) denotes one ensemble member. N denotes the number of ensemble members included in an ensemble set. For example, $C_{crop,k}^t$ denotes function information included in an ensemble to be calculated based on $C_{crop}^t$.

In the ensemble simulation, the crop model processing unit 103 is able to calculate a crop state amount $x_{pheno}^t$ being prediction information independently (or in parallel) for state information $x_{pheno,k}^{t-1}$, function information $C_{crop,k}^t$, and second environment information $\theta 2_{env,k}^t$ (therefore, generate prediction information relating to the observation information Y). For example, the crop model processing unit 103 may predict observation information Y in accordance with Formula 7 (or Formula 5) for each of ensemble members included in N ensemble sets (exemplified in Formula 9) relating to function information $C_{crop}^t$ and second environment information $\theta 2_{env}^t$. The crop model processing unit 103 is able to generate various second environment information $\theta 2_{env}^t$, for example, by processing such as adding a system noise having a predetermined distribution.

The update unit 104 determines whether or not there is newly observed observation information (Step S106). When there is newly observed observation information (YES in Step S106), the update unit 104 updates gene model information and crop model information based on the observation information in accordance with predetermined updating processing (to be described later) (Step S107). The update unit 104 may estimate sequence information that matches the observation information or function information that matches the observation information, based on the updated gene model information and the updated crop model information in accordance with predetermined factor estimation processing (to be described later).

The predetermined factor estimation processing will be described in detail.

Since the gene model information expressed in Formula 3 is model information including uncertainty, it is possible to express a probability with which information is function information $C_{crop}{}^t$, when observation information $Y^t$ at a timing t is given, as a posteriori probability of the observation information $Y^t$, as expressed in Formula 10.

$$p(C_{crop}{}^t | Y^t) \qquad \text{(Formula 10)}.$$

It is possible to implement the processing procedure in accordance with Formula 10 by a processing procedure of acquiring function information $C_{crop}{}^t$ based on observation information $Y^t$ in the processing relating to model information expressed in Formulas 4 to 7. Further, the update unit 104 may also have a function of updating the different second environment information $\theta2_{env}{}^t$ by using observation information Y that is actually observed (specifically, acquiring a priori distribution $p(\theta2_{env}{}^t/Y^t)$, for example.

The predetermined factor estimation processing of estimating sequence information $x_{gene}$ is roughly classified into a direct problem approach and an inverse problem approach. The direct problem approach is a procedure of searching sequence information $x_{gene}$ that is approximate to given observation information $Y^t$, and, for example, there is a processing procedure such as a genetic algorithm. The inverse problem approach is, for example, a procedure of inputting in advance a plurality of patterns in which sequence information $x_{gene}$ appears, and filtering sequence information $x_{gene}$ that gives observation information $Y^t$ (or information similar to observation information $Y^t$) among the patterns. It is possible to implement the inverse problem approach in accordance with a predetermined processing procedure such as sequential Bayesian filtering, data assimilation processing, or a Markov chain Monte Carlo method, for example. The predetermined factor estimation processing is not limited to the above-described processing procedures.

Next, the predetermined updating processing will be described in detail.

The update unit 104 calculates a difference between each piece of function information $C_{crop}{}^t$ (specifically, the priori probability expressed in Formula 10) acquired based on observation information $Y^t$, and function information $C_{crop}{}^t$ calculated in accordance with the gene model information (exemplified in Formula 2 or 3). The update unit 104 updates the gene model information exemplified in Formula 3 by using the difference. The update unit 104 generates information in which gene model information after updating (specifically, information relating to a plant identified by a plant ID), and the plant ID are associated with each other, and stores the generated information in the gene model information storage unit 105. It is possible to calculate a likelihood representing a probability of function information $C_{crop}{}^t$ calculated in accordance with gene model information, and use the likelihood for updating by setting a priori distribution relating to each piece of function information $C_{crop}{}^t$ acquired based on observation information $Y^t$, as a value having a higher probability.

The update unit 104 receives state information $x_{pheno}{}^t$ relating to prediction information predicted for observation information $Y^t$ by the crop model processing unit 103. The update unit 104 further receives observation information $Y^t$ that is actually observed for a plant. The update unit 104 calculates a likelihood representing certainty of a crop state amount $x_{pheno}{}^t$ being prediction information, based on observation information Y and an observation noise w. The update unit 104 updates the crop model information $g_{growth}$ exemplified in Formula 4 (or Formula 6), based on the calculated likelihood. When performing processing in accordance with data assimilation processing, the update unit 104 calculates an error for each of ensemble members included in an ensemble set, and calculates a probability distribution of a crop state amount $x_{pheno}{}^t$ being prediction information under a system noise v. The update unit 104 updates the crop model information $g_{growth}$ by generating crop model information including each piece of function information $C_{crop}$ acquired based on observation information Y and a priori distribution of second environment information $\theta2_{env}$. Alternatively, it is possible to, for example, define a system noise as $v(\rho)$ by using a parameter $\rho$ (hyper parameter) and acquire a prior distribution based on observation information Y similarly. Thus, it is possible to generate crop model information including a system noise in accordance with observation information Y and update the crop model information $g_{growth}$ similarly. The update unit 104 generates information associating crop model information after updating (specifically, information relating to a plant identified by a plant ID) with the plant ID, and store the generated information in the crop model information storage unit 106.

The update unit 104 may specify relevance information including information that matches (or is similar to) observation information $Y^t$ after performing processing in accordance with predetermined updating processing as described above, and present sequence information $x_{gene}$ included in the specified relevance information. In this case, the update unit 104 estimates, based on observation information Y observed for an individual (or a plant), a gene sequence of the individual in accordance with a direct problem approach or an inverse problem approach as described above. The update unit 104 may generate relevance information that associates sequence information $x_{gene}$ representing the estimated gene sequence with the observation information $Y^t$, and store the relevance information in the relevance information storage unit 111.

Processing of estimating sequence information $x_{gene}$ will be described in detail with reference to Formulas 11 and 12 to be described later.

For convenience of description, a timing regarding to sequence information $x_{gene}$ (or observation information $Y^t$) calculated by the update unit 104 is referred to as "t" (where t is a natural number). Further, it is assumed that the observation information storage unit 108 stores observation information $Y^{t+s}$ (where s is a natural number), which is observed later than the timing t on a real-time basis, for example. However, a timing of storing observation information does not need to be on a real-time basis.

The update unit 104 calculates an estimated value of a gene sequence "$x_{gene}{}^{t+s+1}$" at a timing "t+s+1" (where s is a natural number), based on observation information $Y^{t+s}$ at a timing "t+s" (where s is a natural number) later than the timing t, gene model information (exemplified in Formula 2 or 3), and crop model information (exemplified in Formula 4). This processing will be described in detail.

The update unit 104 specifies sequence information $x_{gene}$ (factor information) in a case of observation information $Y^{t+s}$ by performing processing similar to the direct problem approach or the inverse problem approach as described above. Specifically, the update unit 104 calculates a probability (Formula 11) with which sequence information is sequence information $x_{gene}{}^{t+s+1}$ in a case of observation information $Y^{t+s}$ in accordance with crop model information and gene model information.

$$p(x_{gene}^{t+s+1}|Y^{t+s}) \quad \text{(Formula 11)}.$$

Next, the update unit 104 reads relevance information from the relevance information storage unit 111, and reads criteria information from the criteria information storage unit 110. The update unit 104 specifies relevance information (or a value) that satisfies a selection condition represented by the read criteria information among the read relevance information for observation information $Y^{t+s}$ and calculated sequence information $x_{gene}^{t+s+1}$. For convenience of description, this processing is referred to as "specifying processing". When the selection condition is a criterion relating to stability as described above, the update unit 104 specifies relevance information that satisfies a selection condition that a range of observation information $Y^{t+s}$ is within a criteria range among relevance information stored in the relevance information storage unit 111, for example.

The update unit 104 calculates sequence information $x_{gene}^{t+s+1}$ relating to the relevance information storage unit 111 by performing processing similar to the specifying processing for observation information included in specified relevance information (for convenience of description, a set of pieces of the observation information is referred to as a "set Rc"), and observation information $Y^{t+s}$. In this case, the update unit 104 calculates a conditional probability (Formula 12) of sequence information $x_{gene}^{t+s+1}$ when observation information $Y^{t+s}$ and a set Rc are given.

$$p(x_{gene}^{t+s+1}|Y^{t+s},Rc) \quad \text{(Formula 12)}.$$

Therefore, the update unit 104 sets a set Rc to be estimated as sequence information $x_{gene}^{t+s+1}$ based on the criteria information and the relevance information in accordance with the above-described specifying processing. The update unit 104 calculates sequence information $x_{gene}^{t+s+1}$ relating to observation information $Y^{t+s}$ based on the set Rc and an estimated value calculated by using model information.

It is possible to calculate the probability expressed in Formula 12 by analyzing a frequency of appearance of sequence information included in the specified relevance information, for example. Alternatively, the probability may be information that associates sequence information with observation information estimated based on the sequence information.

The update unit 104 may estimate, as sequence information $x_{gene}^{t+s+1}$, sequence information having a largest value among probabilities calculated in accordance with Formula 12.

The update unit 104 estimates sequence information $x_{gene}^{t+1}$ based on observation information $Y^t$ by processing relating to a timing t. The prediction device 101 predicts observation information $Y^t$ based on estimated sequence information $x_{gene}^{t+1}$ (specifically, generates prediction information relating to the observation information). Next, the update unit 104 estimates sequence information $x_{gene}^{t+2}$ based on generated observation information $Y^{t+1}$. Therefore, the update unit 104 estimates sequence information based on observation information received at each timing. Specifically, the update unit 104 estimates, based on a history on observation information relating to an analysis target, a gene sequence of the analysis target.

Figure 3:
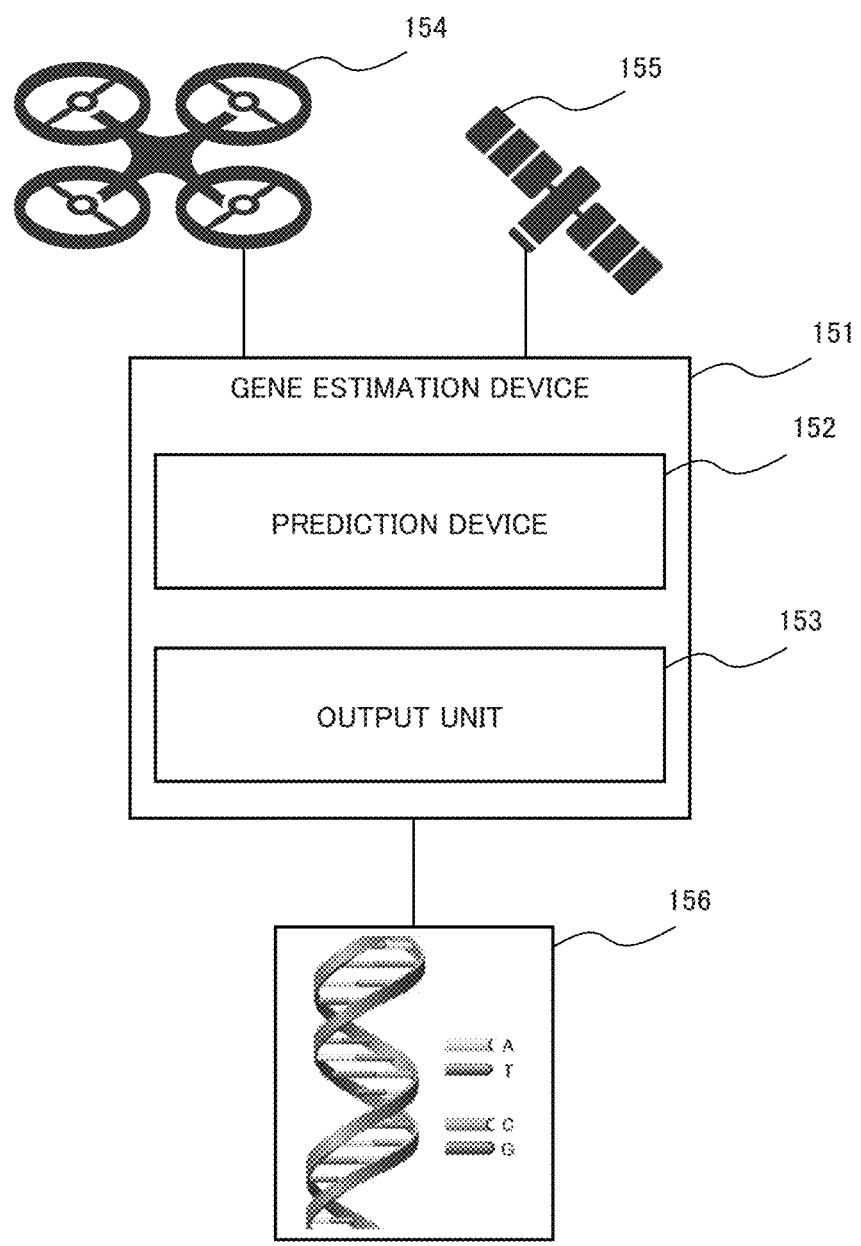
FIG. 3 is a block diagram illustrating a configuration of a genetic estimation device according to the first example embodiment of the present invention.

As exemplified in FIG. 3, a prediction device described in each of example embodiments of the present invention may be included in a genetic estimation device 151. FIG. 3 is a block diagram illustrating a configuration of the genetic estimation device 151 according to the first example embodiment of the present invention.

The genetic estimation device 151 according to the first example embodiment includes a prediction device 152 and an output unit (outputter) 153. The prediction device 152 is implementable by employing a function similar to the function included in the prediction device 101 (or a prediction device 201 to be described later with reference to FIG. 4). The genetic estimation device 151 is communicably connected to a flying object such as a drone 154 or an artificial satellite 155. As described above with reference to FIG. 2, a flying object such as the drone 154 or the artificial satellite 155 includes a sensor for observing a field where a plant (or an individual) is grown. A flying object such as the drone 154 or the artificial satellite 155 transmits, to the genetic estimation device 151, observation information (or environment information) observed by the sensor or the like via a communication network. The genetic estimation device 151 receives the observation information (or the environment information) and inputs these pieces of information to the prediction device 152. The prediction device 152 generates sequence information 156 representing a gene sequence of a plant (or an individual), for example, by performing processing described in each of example embodiments of the present invention. The prediction device 152 inputs the generated sequence information 156 to the output unit 153. The output unit 153 receives the sequence information 156 (e.g., a probability exemplified in Formula 11) and outputs a piece of sequence information 156 having a largest probability among the sequence information 156. Specifically, the output unit 153 receives the sequence information 156 (e.g., a probability exemplified in Formula 11) and outputs at least partial sequence information 156 among the sequence information 156. Therefore, the genetic estimation device 151 is able to estimate a gene sequence based on observation information transmitted by a flying object such as the drone 154 or the artificial satellite 155.

Next, an advantageous effect relating to the prediction device 101 according to the first example embodiment of the present invention will be described.

The prediction device 101 according to the first example embodiment is able to more accurately simulate an analysis target. A reason for this is that it is possible to predict a parameter of a model representing an event, which may be expressed by a gene sequence of an analysis target such as a plant, and simulate an event which occurs in the plant based on the predicted parameter. This reason will be described in detail.

As described in relation to the issue in the present example embodiment, an error occurs between an event predicted by simulation and an event acquired by a sensor or the like. The inventors of the present application have found that one of factors of generating the error is that a gene sequence of an individual is not expressed in model information being a base for the simulation. In view of the above, the inventors of the present application have introduced, to model information, function information $C_{crop}$ representing an event that occurs in relation to sequence information $x_{gene}$ representing a gene sequence, and have expressed a relevance between sequence information $x_{gene}$ and observation information Y via the function information $C_{crop}$. In other words, the prediction device 101 according to the first example embodiment predicts observation information (specifically, generates prediction information relating to the observation information) according to model information (exemplified in Formulas 2 to 7) representing a relevance between sequence information $x_{gene}$ and observation information Y via function information $C_{crop}$. Therefore, since prediction information reflects sequence information $x_{gene}$ as one of factors by the prediction device 101, the prediction device 101 is able to more accurately simulate an analysis target.

Further, the prediction device 101 according to the first example embodiment is able to acquire, in a short period, observation information to be observed for a living body by a gene sequence of the living body. A reason for this is that the prediction device 101 performs simulation based on a gene sequence of an analysis target. Generally, since a period required for simulation relating to an event that occurs in an analysis target is shorter than a period during which the analysis target is actually grown, the prediction device 101 is able to acquire, in a short period, observation information to be observed for a living body by a gene sequence of the living body.

Furthermore, the prediction device 101 according to the first example embodiment is able to estimate a gene sequence of an analysis target based on observation information Y representing an event that is actually observed for the analysis target. A reason for this is that the prediction device 101 specifies sequence information representing a gene sequence being a factor of generating observation information Y by performing processing in accordance with the direct problem approach or the inverse problem approach.

Moreover, when environment information (first environment information or second environment information) is acquired in advance, the prediction device 101 according to the first example embodiment is able to improve harvest efficiency in an environment represented by the environment information. A reason for this is that the prediction device 101 is able to acquire, based on observation information (specifically, prediction information) predicted for a plant (or an individual), information relating to growth of the plant. Specifically, since the prediction device 101 predicts, based on sequence information of a plant (or an individual) and environment information, observation information when the plant (or the individual) is grown (specifically, generates prediction information), a user is able to specify, based on the prediction information, a plant (or an individual) appropriate for the environment information before the plant is grown.

In addition, even when sequence information relating to a plant (or an individual) is not acquired in advance, the prediction device 101 according to the first example embodiment is able to improve harvest efficiency in an environment represented by environment information. A reason for this is that a user is able to specify, based on prediction information and sequence information relating to a plant (or an individual) of the prediction device 101, a plant (or an individual) appropriate for an environment represented by the environment information.

Second Example Embodiment

Next, a second example embodiment according to the present invention will be described.

Figure 4:
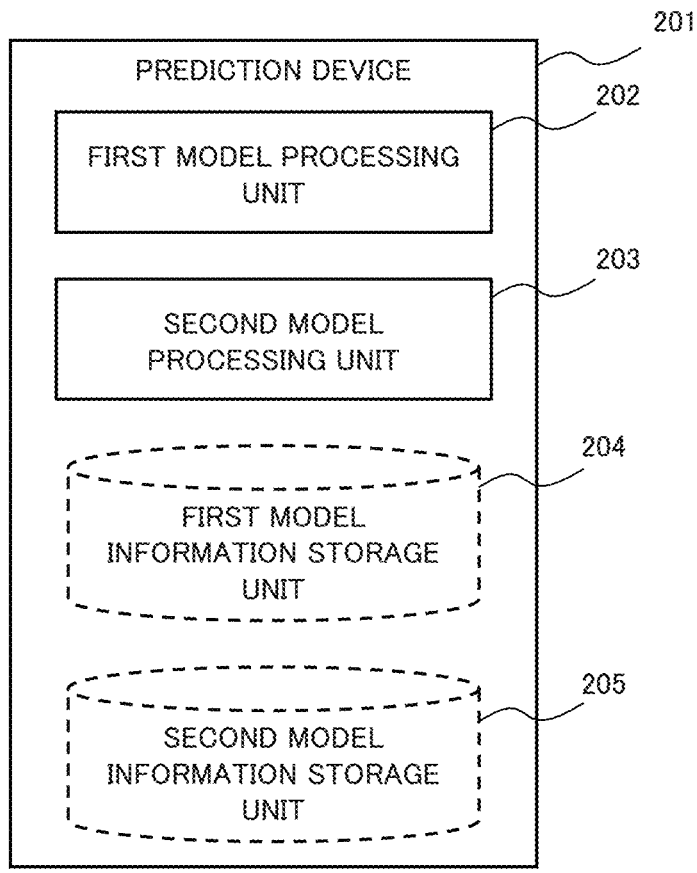
FIG. 4 is a block diagram illustrating a configuration of a prediction device according to a second example embodiment of the present invention.

A configuration of the prediction device 201 according to the second example embodiment of the present invention will be described in detail with reference to FIG. 4. FIG. 4 is a block diagram illustrating a configuration of the prediction device 201 according to the second example embodiment of the present invention.

The prediction device 201 according to the second example embodiment includes a first model processing unit (first model processor) 202 and a second model processing unit (second model processor) 203. The prediction device 201 may further include a first model information storage unit 204 and a second model information storage unit 205.

In the following description, for convenience of description, it is assumed that an analysis target is a plant (crop) to be grown in a field. The analysis target, however, is not limited to a plant, and any living body is applicable.

The first model information storage unit 204 stores first model information (e.g., "gene model information") representing a relevance between sequence information representing a gene sequence and function information relating to a function potentially expressed by the gene sequence, as described with reference to FIG. 1. The first model information may be information representing a relevance among environment information representing an environment around a living body having the gene sequence, the sequence information, and the function information. The second model information storage unit 205 stores second model information (e.g., crop model information) in which a relevance in a state of the living body at a plurality of timings is expressed via the function information, as described with reference to FIG. 1.

Figure 5:
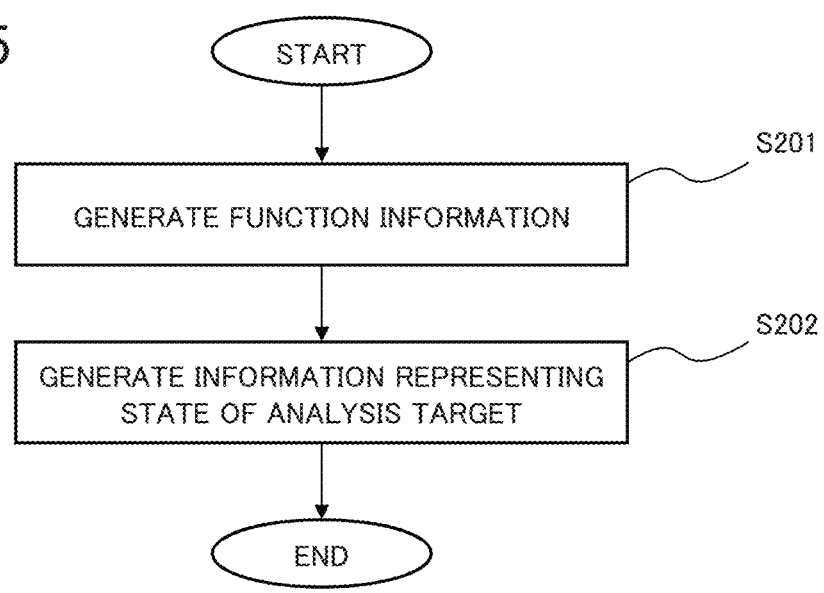
FIG. 5 is a flowchart illustrating a flow of processing in the prediction device according to the second example embodiment.

Next, processing of the prediction device 201 according to the second example embodiment of the present invention will be described in detail with reference to FIG. 5. FIG. 5 is a flowchart illustrating a flow of processing in the prediction device 201 according to the second example embodiment.

The first model processing unit 202 receives sequence information representing a gene sequence of an analysis target such as a plant (or an individual). The first model processing unit 202 reads first model information (exemplified in Formula 2 or 3) stored in the first model information storage unit 204. The first model processing unit 202 generates function information relating to an analysis target by applying, to the received sequence information, processing represented by the first model information (Step S201). The first model processing unit 202 inputs the generated function information to the second model processing unit 203. Processing in Step S201 is, for example, processing similar to the processing as described with reference to Step S104 in FIG. 2.

Next, the second model processing unit 203 receives the function information and information representing a state (hereinafter, referred to as a "first state") of the analysis target at a first timing. The second model processing unit 203 receives, from an external device, environment information relating to an environment around the analysis target. The second model processing unit 203 reads second model information (e.g., crop model information exemplified in Formula 4 or 6) stored in the second model information storage unit 205. The second model processing unit 203 calculates information representing a state (hereinafter, referred to as a "second state") of the analysis target at a second timing by applying, to the function information and the first information, processing represented by the second model information (Step S202). Processing in Step S201 is, for example, processing similar to the processing as described with reference to Step S105 in FIG. 2.

The first model information storage unit 204 is implementable by employing a function similar to the function of the gene model information storage unit 105 (FIG. 1) according to the first example embodiment. The second model information storage unit 205 is implementable by employing a function similar to the function of the crop model information storage unit 106 (FIG. 1) according to the first example embodiment. The first model processing unit 202 is implementable by employing a function similar to the function of the gene model processing unit 102 (FIG. 1) according to the first example embodiment. The second model processing unit 203 is implementable by employing a function similar to the function of the crop model processing unit 103 (FIG. 1) according to the first example embodiment. Therefore, the prediction device 201 is implementable by employing a function similar to the function of the prediction device 101 (FIG. 1) according to the first example embodiment.

Next, an advantageous effect relating to the prediction device 201 according to the second example embodiment of the present invention will be described.

The prediction device 201 according to the present example embodiment is able to more accurately simulate an analysis target. A reason for this is that it is possible to predict a parameter included in model information representing an event that may be expressed with respect to a gene sequence of an analysis target such as a plant, and simulate an event which occurs relating to the plant, based on the predicted parameter. This reason will be described in detail.

As described in relation to the issue in the present example embodiment, the inventors of the present application have found that one of factors of generating an error in simulation is that a gene sequence of a plant (or an individual) is not expressed in model information being a base for the simulation. In view of the above, the inventors of the present application have introduced, to model information, function information $C_{crop}$ representing an event that occurs in relation to sequence information $x_{gene}$ representing a gene sequence, and have expressed a relevance between sequence information $x_{gene}$ and state information $x_{pheno}$ via the function information $C_{crop}$. In other words, the prediction device 201 according to the second example embodiment calculates a second state relating to an analysis target in accordance with model information and the like (exemplified in Formulas 2 to 7) representing a relevance between sequence information $x_{gene}$ and state information $x_{pheno}$ via function information $C_{crop}$. Therefore, since the second state reflects sequence information $x_{gene}$ as one of factors by the prediction device 201, the prediction device 201 is able to more accurately simulate an analysis target.

(Hardware Configuration Example)

A configuration example of hardware resources that achieve a prediction device or a gene estimation device according to each example embodiment of the present invention using a computer processing device (information processing device, compute) will be described. However, the prediction or the gene estimation device may be achieved using physically or functionally at least two calculation processing devices. Further, the prediction device or the gene estimation device may be achieved as a dedicated device.

Figure 6:
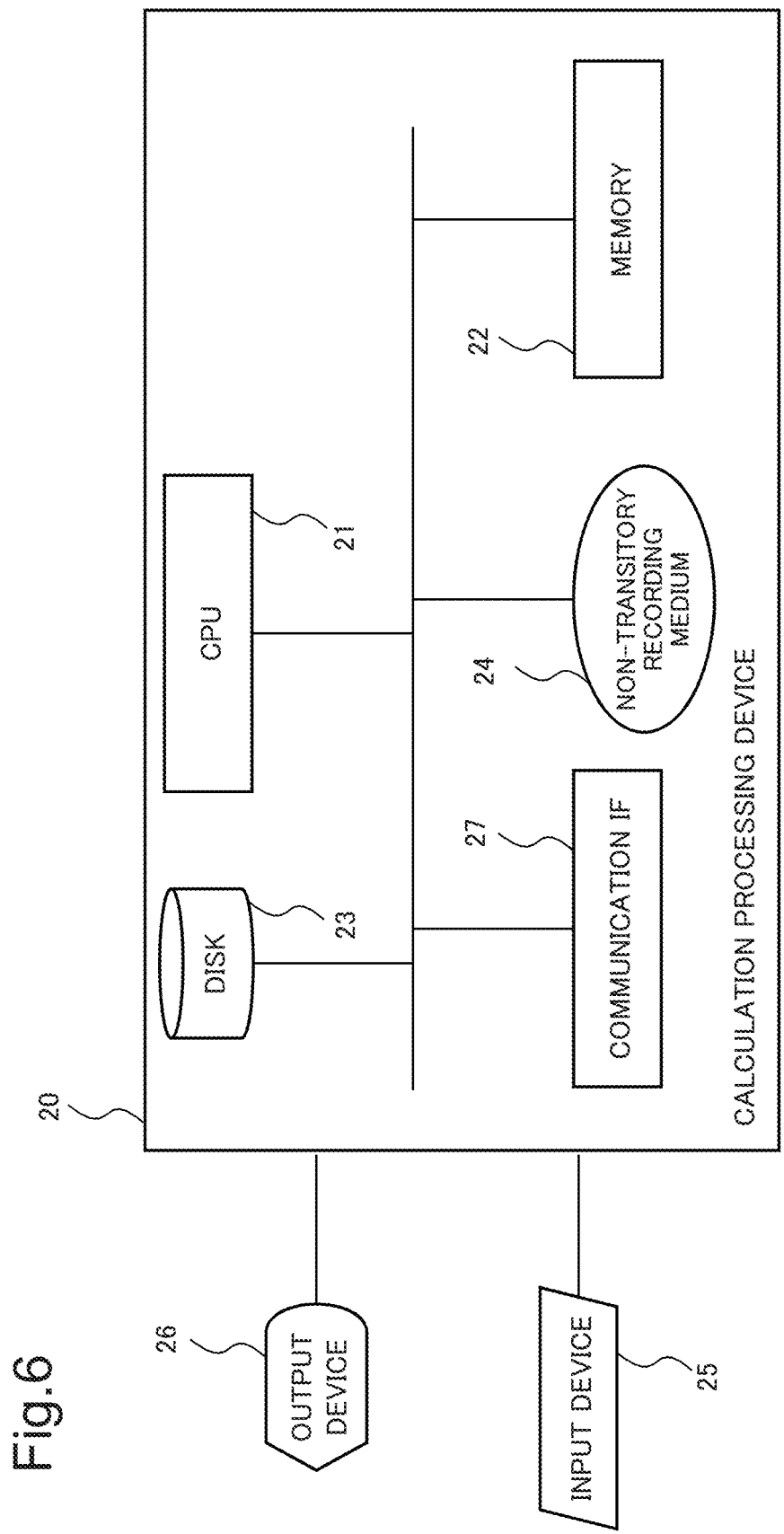
FIG. 6 is a block diagram schematically illustrating a hardware configuration of a calculation processing device capable of achieving a prediction device or a gene estimation device according to each example embodiment of the present invention.

FIG. 6 is a block diagram schematically illustrating a hardware configuration of a calculation processing device capable of achieving a prediction device or a gene estimation device according to each example embodiment of the present invention. A calculation processing device 20 includes a central processing unit (hereinafter, referred to as "CPU") 21, a memory 22, a disk (disc) 23, a non-transitory recording medium 24, and a communication interface (hereinafter, referred to as "communication I/F") 27. The calculation processing device 20 may connect an input device 25 and an output device 26. The calculation processing device 20 can execute transmission/reception of information to/from another calculation processing device and a communication device via the communication I/F 27.

The non-transitory recording medium 24 is, for example, a computer-readable Compact Disc, Digital Versatile Disc. The non-transitory recording medium 24 may be Universal Serial Bus (USB) memory, Solid State Drive or the like. The non-transitory recording medium 24 allows a related program to be holdable and portable without power supply. The non-transitory recording medium 24 is not limited to the above-described media. Further, a related program can be carried via a communication network by way of the communication I/F 27 instead of the non-transitory recording medium 24.

In other words, the CPU 21 copies, on the memory 22, a software program (a computer program: hereinafter, referred to simply as a "program") stored in the disk 23 when executing the program and executes arithmetic processing. The CPU 21 reads data necessary for program execution from the memory 22. When display is needed, the CPU 21 displays an output result on the output device 26. When a program is input from the outside, the CPU 21 reads the program from the input device 25. The CPU 21 interprets and executes a prediction program (FIG. 2 or FIG. 5) present on the memory 22 corresponding to a function (processing) indicated by each unit illustrated in FIG. 1, FIG. 3, or FIG. 4 described above. The CPU 21 sequentially executes the processing described in each example embodiment of the present invention.

In other words, in such a case, it is conceivable that the present invention can also be made using the prediction program. Further, it is conceivable that the present invention can also be made using a computer-readable, non-transitory recording medium storing the prediction program.

The present invention has been described using the above-described example embodiments as example cases. However, the present invention is not limited to the above-described example embodiments. In other words, the present invention is applicable with various aspects that can be understood by those skilled in the art without departing from the scope of the present invention.

REFERENCE SIGNS LIST

101 prediction device
102 gene model processing unit
103 crop model processing unit
104 update unit
105 gene model information storage unit
106 crop model information storage unit
107 function information storage unit
108 observation information storage unit
109 environment information storage unit
110 criteria information storage unit
111 relevance information storage unit
151 gene estimation device
152 prediction device
153 output unit
154 drone
155 artificial satellite
156 sequence information
201 prediction device
202 first model processing unit
203 second model processing unit
204 first model information storage unit
205 second model information storage unit
20 calculation processing device
21 CPU 22 memory
23 disk
24 non-transitory recording medium
25 input device
26 output device
27 communication IF

The invention claimed is:

1. A prediction device comprising:
a memory for storing instructions; and
a processor connected to the memory and configured to execute the instructions to:
generate function information for a gene sequence of a living body to be an analysis target based on first model information representing a relevance between sequence information and the function information, the sequence information representing the gene sequence of the analysis target, the function information representing a function potentially expressed by the gene sequence,
generate prediction information representing observation information predicted for the analysis target based on second model information and the function information, the second model information representing a relevance among the function information of the living body, environment information representing an environment around the living body, and the observation information observed for the living body, the function information being generated for the gene sequence of the analysis target,
generate prediction information representing predictive observation information for the target analysis based on third model information representing a relevance between a state of the living body and observation information observed for the living body, and
update the second model information based on a difference between observation information observed for the analysis target and the generated prediction information.

2. The prediction device according to claim 1, wherein the processor is configured to execute the instructions to estimate the function information in case of generating the prediction information by using the updated second model information and update the first model information based on a difference between the estimated function information and the function information generated based on the first model information.

3. The prediction device according to claim 1, wherein the processor is configured to execute the instructions to specify the sequence information associated with the observation information for the analysis target based on relevance information associating the sequence information for the living body with observation information observed for the living body.

4. The prediction device according to claim 3, wherein the processor is configured to execute the instructions to specify relevance information satisfying a predetermined condition of similarity degree to the observation information for the analysis target among the relevance information and specify the sequence information included in the specified relevance information.

5. The prediction device according to claim 3, wherein the processor is configured to execute the instructions to generate the relevance information associating the sequence information specified for the analysis target with the observation information for the analysis target.

6. A gene estimation device comprising:
the prediction device according to claim 4, wherein the processor is configured to execute the instructions to output, at least, partial sequence information among the specified sequence information.

7. A prediction method, by an information processing device, comprising:
generating function information for a gene sequence of a living body to be an analysis target based on first model information representing a relevance between sequence information and the function information, the sequence information representing the gene sequence of the analysis target, the function information representing a function potentially expressed by the gene sequence;
generating prediction information representing observation information predicted for the analysis target based on second model information and the function information, the second model information representing a relevance among the function information of the living body, environment information representing an environment around the living body, and the observation information observed for the living body, the function information being generated for the gene sequence of the analysis target;
generating prediction information representing predictive observation information for the target analysis based on third model information representing a relevance between a state of the living body and observation information observed for the living body; and
updating the second model information based on a difference between observation information observed for the analysis target and the generated prediction information.

8. A non-transitory recording medium storing a prediction program comprising instructions that, when executed by a computer, cause the computer to:
generate function information for a gene sequence of a living body to be an analysis target based on first model information representing a relevance between sequence information and the function information, the sequence information representing the gene sequence of the analysis target, the function information representing a function potentially expressed by the gene sequence;
generate prediction information representing observation information predicted for the analysis target based on second model information and the function information, the second model information representing a relevance among the function information of the living body, environment information representing an environment around the living body, and the observation information observed for the living body, the function information being generated for the gene sequence of the analysis target by the first model processing function;
generate prediction information representing predictive observation information for the target analysis based on third model information representing a relevance between a state of the living body and observation information observed for the living body; and
update the second model information based on a difference between observation information observed for the analysis target and the generated prediction information.

* * * * *